United States Patent [19]

Hazel et al.

[11] 4,051,842
[45] Oct. 4, 1977

[54] ELECTRODE AND INTERFACING PAD FOR ELECTRICAL PHYSIOLOGICAL SYSTEMS

[75] Inventors: Patrick Michael Hazel; Roberta Evans Wells, both of Littleton, Colo.

[73] Assignee: International Medical Corporation, Englewood, Colo.

[21] Appl. No.: 613,520

[22] Filed: Sept. 15, 1975

[51] Int. Cl.² ............................................. A61B 5/04
[52] U.S. Cl. .......................... 128/2.06 E; 128/2.1 E; 128/417; 128/DIG. 4
[58] Field of Search ............... 128/2.06 E, 2.1 E, 404, 128/410, 411, 416–418, DIG. 4

[56] References Cited

U.S. PATENT DOCUMENTS

| | | | |
|---|---|---|---|
| 2,047,308 | 7/1936 | Chapman | 128/417 |
| 2,555,037 | 9/1951 | Jensen | 128/417 |
| 3,085,577 | 4/1963 | Berman et al. | 128/418 |
| 3,170,459 | 2/1965 | Phipps et al. | 128/2.06 E |
| 3,380,445 | 4/1968 | Frasier | 128/2.06 E |
| 3,496,929 | 2/1970 | Domingues | 128/2.06 E |
| 3,587,565 | 6/1971 | Tatoian | 128/2.06 E |
| 3,599,629 | 8/1971 | Gordy | 128/2.06 E |
| 3,805,769 | 4/1974 | Sessions | 128/2.06 E |
| 3,830,229 | 8/1974 | Johnson | 128/2.06 E |
| 3,845,757 | 11/1974 | Weyer | 128/2.06 E |

FOREIGN PATENT DOCUMENTS 54,063  2/1967  Germany ..................... 128/2.06 E

*Primary Examiner*—Robert W. Michell
*Assistant Examiner*—Lee S. Cohen
*Attorney, Agent, or Firm*—John E. Reilly

[57] ABSTRACT

An electrical interconnection is provided between a patient and physiological sensing or monitoring equipment. A permanent electrode is formed with a thin flexible housing which encases an electrical connector such as a pellet or nodule so that a portion of that connector is externally exposed on one surface. A disposable pad formed of a thin flexible base frame has a central bore and a double-faced adhesive disc on one side for attachment of the electrode surface containing the connector and concurrently retaining a conductive gel within the disposable pad for electrical communication with the electrode conductor. The adhesive on the opposite surface of the disposable pad is adapted to secure the pad to a selected area of the skin of the patient.

11 Claims, 8 Drawing Figures

U.S. Patent  Oct. 4, 1977  Sheet 1 of 2  4,051,842
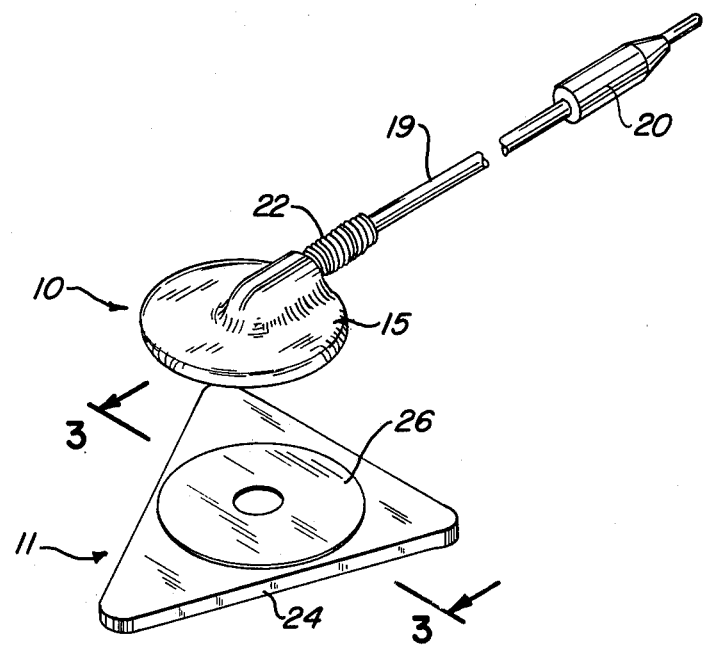
Fig_1
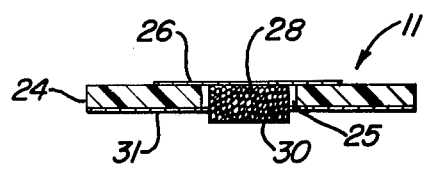
Fig_3
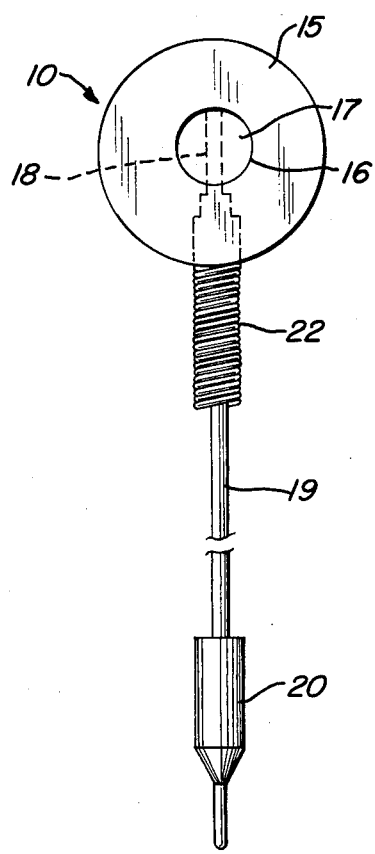
Fig_2
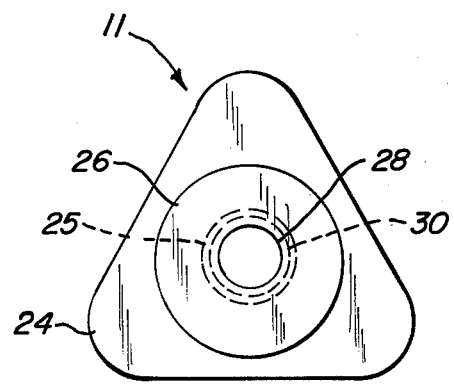
Fig_4

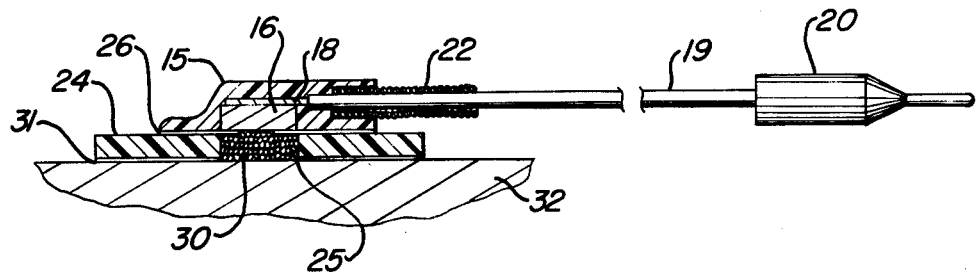
Fig _ 5
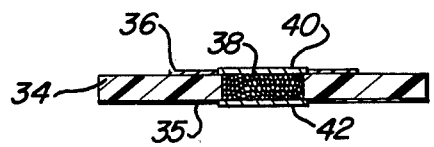
Fig _ 6
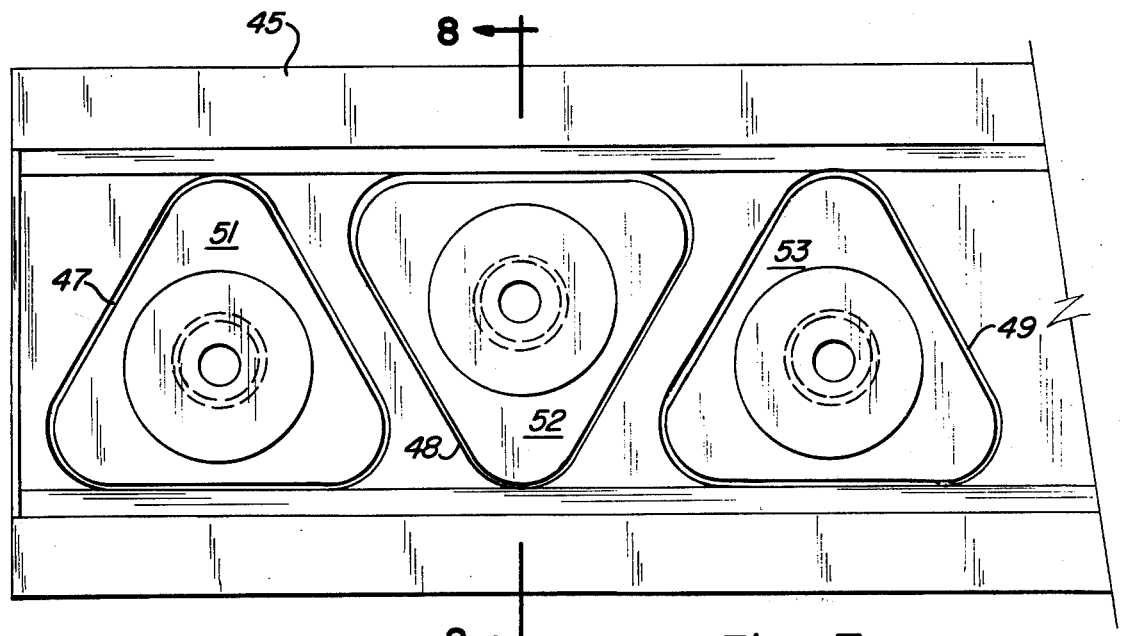
Fig _ 7
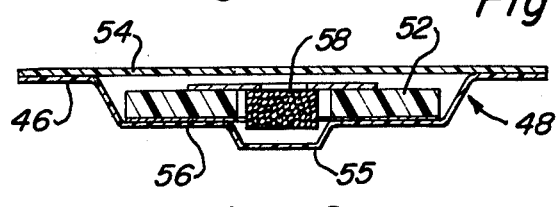
Fig _ 8

ELECTRODE AND INTERFACING PAD FOR ELECTRICAL PHYSIOLOGICAL SYSTEMS

BACKGROUND OF THE INVENTION

The present invention relates to devices for providing an electrical interface between a patient and an electrical physiological monitoring, sensing or measuring equipment. More particularly, the present invention relates to apparatus capable of effecting a temporary electrical interconnection between the skin surface of a patient and the input connection for electrical medical data acquisition equipment and is particularly useful in establishing a secure but adaptably flexible electrical interface between a selected area of the skin and the input for electrical physiological measuring, sensing or detecting systems such as electrocardiograms and other electrical monitoring systems of the type which require a low, constant resistance interconnection with a patient.

A variety of devices have been developed in the past for acquiring medical data on a patient from electrical parameters associated with the patient. Some devices sense the electrical conductivity within the patient while others measure various other parameters including internal resistance and the like. Such medical electrical measurement or testing systems are necessarily sensitive because of the low levels of electrical activity involved and require relatively constant and low resistance interfacing with the skin of the patient. It was early recognized that merely strapping an electrical connector to the skin of a patient would produce an unpredictable interface resistance thus discounting the measurement acquired. An early practice has been to specially treat the skin area of the patient so as to reduce the electrical resistance at the surface and to include a conductive gel between the electrode and the skin of the patient to further reduce the interface resistance. Thus a variety of devices have been developed for the purpose of combining the adhering functions and the conductive gel retaining functions in a common housing. For instance, Phipps et al No. 3,170,459 shows an electrode combination formed of a plurality of bonded insulator layers with an electrode connector button exposed to a cavity in which gel can be inserted. Similar unitary electrode connector assemblies have been shown in Mason U.S. Pat. No. 3,518,984, Yuan U.S. Pat. No. 3,572,323 and Weyer U.S. Pat. No. 3,845,757. An electrode with a snap-on connector and an oversized conductive gel retaining disc for filling the cavity under the connector in response to attachment compression is shown in U.S. Pat. No. 3,882,853 by Gofman et al.

However, the aforementioned prior art connectors are difficult to recharge or clean and sterilize for reuse particularly where an internal cavity is incorporated. Ultrasonic cleaning of the gel cavity type electrode is reasonably satisfactory but necessarily delays availability of the electrodes for further use. One approach that has been suggested for avoiding delays in electrode availability is to use disposable electrodes such as in Sessions U.S. Pat. No. 3,805,769 wherein a bonded disc arrangement with a snap-type of connector is formed as a unit and thrown away after utilization. However, it is important that the connector button for the electrode exhibit high quality electrical interfacing characteristics, silver and silver chloride combinations being particularly attractive in this regard. Thus the use of such materials for the electrode is prohibitively expensive for inclusion in a disposable application. Furthermore, although many of the prior art interfacing electrode assemblies are reasonably satisfactory for static measurement, it is frequently important that the electrical measurements be continuously maintained even during relatively violent physical activity in order to acquire meaningful data on the patient. Security of the interface connection under such conditions is vital since a loose connection will result in noisy readings and useless data. Beyond this, there is a need for an electrical interfacing apparatus which can remain attached to a bed-ridden patient for continuous monitoring of vital functions and the like.

Therefore, there has been a continuing need for an electrical interfacing arrangement between a patient and medical sensing or monitoring apparatus which establishes a reliably secure attachment while accommodating movement of the patient without detracting from the constant, minimal resistance at the interface. Furthermore, there is a continuous need for an interfacing arrangement which permits retention of the more expensive electrode so that it can be quickly and effectively prepared for further use while allowing disposal of the less expensive conductive gel.

Summary of the Invention

The present invention resides in an electrode and interfacing pad arrangement which defines an electrical interconnection between a patient and electrical medical measurement or sensing equipment so as to accommodate flexing movement of the patient and minimizes potential loose connections or unintended removal. The electrode assembly in accordance with the present invention is formed of a flexible housing of insulating material which has a flat surface removably securing to the patient. An electrical conductor, pellet or button is embedded within the insulator housing so that a surface thereof is externally exposed through the housing as part of the interior portion of the housing flat surface that is attached to the patient. A suitable conductive lead is then arranged to provide electrical communication between the conductor button and the other electrical medical equipment by extension through yet another surface of the housing.

The electrical interfacing in accordance with this invention is completed by a disposable pad assembly which has a base frame of a flexible, closed cell material with this base frame being formed of relatively thin configuration with opposite flat surfaces. A bore extends through the pad assembly, and an adhesive on one side surrounds the bore and is arranged in conformity with the configuration of the electrode flat surface for retaining it in proximity to the base frame so that the electrical conductor overlays the pad bore. A second adhesive surface substantially covers all of the opposite base frame surface around the bore so as to retain the base frame to the patient. The base frame bore is filled with an electrically conductive gelatin so as to complete a relatively constant, low resistance electrical circuit between the area of the patient beneath the bore and the electrical conductor surface. By this configuration, the electrode can be easily cleaned such as by wiping with alcohol, since all of the surfaces thereof are substantially flat and the pads thrown away and replaced after use.

The disposable interfacing pad can be formed in a triangular configuration to optimize the number of electrodes which can be placed on a given skin surface area of the patient. Further, the electrode can be configured of a relatively low, rounded edge profile with a smaller outer perimeter than the outer perimeter of the pad, thus further reducing the prospect of accidental removal or loosening of the electrode such as by movement of an active patient or a bed-ridden patient. The gel can be retained within the pad by means of an open-celled carrier or retained between thin gel permeable discs such as of felt or the like. Still further, the triangular configuration of the pad permits optimization of packaging in protective cartridges for storage and transportation prior to use.

An object of the present invention is to provide a novel and improved electrical interface between a patient and electrical medical equipment.

Another object of the present invention is to provide a novel and improved reliably secure electrical interface between a patient and medical equipment with relatively constant, low electrical resistance.

Yet another object of this invention is to provide a highly flexible electrical interface between a patient and electrical medical equipment which can accommodate movement of the patient without significant variations in the interface resistance or prospects of unintended loosening or detachment of the electrode.

A further object of the present invention is to provide an electrical interface between the patient and electrical medical equipment which permits disposal of the low cost conductive gel retaining portion and retention of the more expensive electrode in a manner which permits rapid sterilization of the electrode for reuse.

The foregoing and other objects, features and advantages of the present invention will be more apparent in view of the following detailed description of exemplary preferred embodiments.

BRIEF DESCRIPTION OF THE DRAWINGS

FIG. 1 is a perspective view of an electrode and an interfacing pad assembly in accordance with the present invention.

FIG. 2 is a bottom plan view of the electrode assembly of FIG. 1.

FIG. 3 is a section view of the interfacing pad of FIG. 1.

FIG. 4 is a top plan view of the interfacing pad of FIGS. 1 and 3.

FIG. 5 is a side partially sectioned view of an attached electrode and interfacing pad arrangement.

FIG. 6 is a side section view of an alternate arrangement of the interfacing pad structure.

FIG. 7 is a top view of a storage tray adapted for retention of a plurality of the interfacing pads; and FIG. 8 is a section view taken along lines 8—8 of FIG. 7.

DETAILED DESCRIPTION OF THE PREFERRED EMBODIMENTS

FIG. 1 shows a perspective view of a relatively permanent electrode assembly 10 and disposable interfacing pad 11 as it would be positioned immediately prior to attachment to a patient. Essentially, electrode housing 10 is a relatively permanent structure which is reusable whereas interfacing pad 11 is typically discarded after use. A sectioned view of the complete attachment of both assemblies to a patient is shown in FIG. 5.

Electrode assembly 10 includes a circular disc-like main frame or housing 15 which is formed in a thin, flexible configuration but which has embedded therein a button-like electrical conductor or pellet 16 which forms the interior portion of the lower flat surface of housing 15. That is, housing 15 is typically formed of a rubber or rubber-like material, a flexible plastic such as a urethane polymer, or the like. The conductor 16 is formed of materials which (1) have good electrical conductivity characteristics, (2) have relatively low constant electrical resistance at the interfacing surface, and (3) are relatively inert chemically to the interface environment. In this regard, satisfactory results are obtained by fabricating conductor 16 as a silver/silver chloride composition pellet, such as, sintered silver/silver chloride or a silver central portion plated with a foil of silver chloride or the like. A conductor wire 18 is bonded as by welding, soldering, metalized epoxy bonding or the like to the interior surface of pellet 16 and passes through an external lead 19 to a conventional probe 20 for attachment to electrical medical measuring or sensing equipment [not shown]. Note that wire 18 can be compressively bonded into pellet 16 when it is formed if separate bonding is not desired. A stress relief coil 22 can be included at the leading edge of conductor wire 19 and partially embedded in housing 15.

FIG. 2 shows a bottom plan view of the electrode assembly 10. In FIG. 2, it can be seen that the lower surface 17 of pellet 16 forms the interior portion of the bottom flat surface of housing 15 and is flush mounted with that surface. Accordingly, the entire electrode assembly 10 can be quickly cleaned and sterilized immediately subsequent to use, such as, by an alcohol cleaning process and is therefore almost immediately available for repeated usage.

The disposable interfacing pad assembly 11 of the FIG. 1 embodiment is illustrated in the section view of FIG. 3 taken along lines 3—3 of FIG. 1. This pad includes a triangularly shaped base frame 24 which is preferably of a closed cell, highly flexible foam material. Typically, base frame 24 will be between 1/16 and 1/8 inches thick. One material found to be particularly suitable for base frame 24 is Volara polyethylene available from the Voltek Corporation rated at 4 pounds per cubic foot, 60 pores per inch which molds into a skinned (i.e. high density, glossy surface) closed cell, moisture resistant form in use. However, polyurethane has also been found to be generally acceptable as would be any material which results in a thin, flexible, chemically inert and closed cell structure. Preferably, the outer triangular perimeter of base frame 24 is formed in an equilateral triangle of about 1.5 to 2.5 inches on each side with rounded corners as shown. This configuration permits maximum placement of electrodes within a minimal area on a patient while still retaining the security of attachment.

The base frame 24 has a central bore 25 therethrough which is typically on the order of 0.50 to 0.75 inches in diameter and has an adhesive disc 26 which has double adhesive surfaces thereon attached to the upper side of base frame 24. The outer perimeter of disc 26 conforms with the outer perimeter of electrode housing 15 so as to provide a substantial adhering surface therebetween. Still further, the interior of double adhesive disc 26 has a hole 28 therethrough which is smaller than the bore 25 and slightly smaller than the gel carrier 30. Gel carrier 30 is preferably formed of an open cell plastic foam and typically saturated with conventional conductive gel such as a sodium chloride based electrolyte, commercially available such gels being the pastes or creams offered under tradenames of "EKG-Sol," "Redux," "GE Jel," and the like. However, carrier 30 is thicker than base frame 24 (up to twice the thickness of frame 24 having been found to be satisfactory) but of slightly narrower width than bore 25 as illustrated in FIG. 3. This is particularly evident in the top view of assembly 11 as presented in FIG. 4. Accordingly, double adhesive sided disc 26 provides the concurrent functions of retaining conductive gel carrier 30 in place relative to base frame 24 while further permitting passage of carrier 30 through opening 28 thereof to surface 17 of conductor pellet 16. Further, the entire lower surface 31 of base frame 24 has an adhesive coating thereon for attachment to the patient. The various adhesive surfaces mentioned are composed of suitable conventional materials, examples being non-toxic pressure sensitive coatings of a resin solution of a low molecular weight acrylic polymer, hypoallergenic acrylate based adhesives, etc.

The complete attachment of electrode assembly 10 and interfacing pad assembly 11 to the surface area 32 of a patient is shown in the partially sectioned view of FIG. 5. By dimensioning the gel carrier 30 so that it is thicker than base frame 24 but of a smaller diameter than bore 25 through base frame 24, the attachment of both assemblies to the patient and each other via the adhesive interfaces of disc 26 and surface 31 compresses pad 30 so as to fill the cavity of bore 25 shown in FIG. 5 and further force the upper surface of carrier 30 against the lower surface 17 of pellet 16 so as to insure a constant, low resistance interface between skin surface 32 and electrical conductor pellet 16. This arrangement further minimizes any deterioration of the adhesive security between the elements since any gel oozing is substantially prevented. Still further, by dimensioning double adhesive disc 26 and housing 15 to be in the range of 1.0 to 1.25 inches in diameter, the outer edges of housing 15 will be inwardly displaced from the outer perimeter edges of triangular base frame 24 thus forming an overall concave configuration which will minimize the prospect of unintended removal or loosening of the completed assembly from the patient. By maintaining base frame 24 and housing 15 with minimal thicknesses wherever possible, the entire assembly is sufficiently flexible to conform to movement of the skin surface area 32 without loss of adhesion or any substantial variation in the resistance at this interface. The triangular pad 24 is preferably of a closed cell urethane plastic or foam whereas the gel carrier 30 is an open cell urethane foam. The electrode 16 is preferably sintered or compressed silver/silver chloride or a silver chloride coated or thin plated silver conductor of about 0.050 inch thickness.

A prospective alternate arrangement for the disposable interfacing pad is shown in FIG. 6. As with FIGS. 3 and 4, the base frame 34 is preferably triangular shaped and has an adhesive coating 35 on the lower side thereof and a disc 36 on the upper surface which is adhesively coated on both sides. However, the conductive gelatin 38 is retained between two separate gel saturable pads 40 and 42 so that the central bore through disc 36 is greater than the central bore through base frame 34. For instance, if bore or cavity 38 has a 0.5 inch diameter, pads 40 and 42 are typically of 9/16 inch diameter. The inner area or chamber 38 can be completely gelatin filled or can be filled with an open celled carrier similar to that mentioned previously except closely conforming to or slightly greater than the dimensions of the central bore through base frame 34. Pads 40 and 42 are of felt, loosely woven material or the like.

FIGS. 7 and 8 illustrate a storage and shipment tray 45 which has a substantially flat plate 46 from which depends a plurality of triangularly shaped depressions or cells 47–49. These cells each contain one triangular interfacing pad such as 51–53. The section view of FIG. 8 which is taken along lines 8—8 of FIG. 7 illustrates a typical cross-section of a retaining cell such as cell 48. A thin protective foil 54 is placed over the entire tray. Each cell includes a lower depression or well area 55 to accommodate the central gel carrier 58 so that it is clear of the sidewalls of tray 45 and also clear of the protective foil 54. The disposable pad 52 can be adhered to the walls of cell 48 via adhesive layer 56 which can be the same as the lower adhesive layers 31 described previously for FIGS. 1–5. Thus by fabricating tray 45 from molded, low cost plastics, the disposable pads can be retained in place by their own adhesive surfaces and yet stored so that the gel carriers 58 are not in contact with any surface other than the retaining disc. The protective foil 54 further prevents drying of the gelatin in carrier 58.

In fabricating the pad, its triangular shape is preferably an equilateral triangle developed on the perimeter of a 1.5 to 3.0 inch diameter. The gel is conventional and preferably has good hygroscopic characteristics. That is, it typically includes hygroscopic agents for preventing or reducing dry-out. The dry-out of the conductive gel is further reduced by constructing base frame 24 of closed cell materials as mentioned thereby preventing moisture migration from the gel in carrier 30 into the base frame 24. The gel, paste or cream used can also include fungicides and bacteriacides as is known in the art. Typically, skin preparation techniques may be applied prior to attachment of the electrodes as is also known in the art. Note that peelback-type protective strips can be included on one or both of the external adhesive sufaces of the disposable pad if this should be desirable for individual pad storage or storage within a tray as shown in FIGS. 7 and 8.

Disc 26 can be fabricated from commercially available double adhesive surfaced strips of about writing paper thickness (about 0.005 inches), one example being the product produced by Remco Tape Products Company of Los Angeles, California which has silicon coated protective paper foils over the adhesive surfaces. Thus disc 26 can be cut from such materials and one protective covering removed for attaching disc 26 to base frame 24 leaving the other protective covering in place for removal immediately prior to use with electrode assembly 10. The lower surface of base frame 24 has adhesive layer 31 applied thereto from any material which is FDA approved for non-toxic, medical applications. These adhesives are typically available from transfer tapes such as part number 1552 produced by the Medical Products Division of Minnesota Mining and Manufacturing Company of St. Paul, Minnesota. A particularly attractive example of materials for carrier 30 is the Scott Industrial Foam rated at 40 pores per inch from the Foam Division of the Scott Paper Company of Chester, Pennsylvania. This is a reticulated polyurethane foam which provides a highly flexible structure with continuous open passageways therethrough as a result of well controlled reticulation and bubble size. The carrier thereby exhibits excellent gel penetration characteristics.

In constructing electrode assembly 10, it has been found that treatment of the surface of pellet 16 with a primer and molding of housing 15 of a solid polyurethane results in a rugged, highly flexible structure with excellent adherence between housing 15 and electrical connector pellet 16 despite stretching and flexing of housing 15. This bonding is particularly advantageous in assuring the integrity of assembly 10 for quick cleaning and re-use purposes. It has also been found that forming housing 15 so that it is about 1/16 inch thick at the beginning of the curved edges and tapered upward to about one-eighth inch at the center or around the raised area for accommodating lead 19 and stress relief coil 22, housing 15 will follow the flexing movements of pad assembly 11 without loss of the security of attachment and without resistance modulation at the interface.

Although the present invention has been described with particularity relative to the foregoing detailed description of exemplary preferred embodiments, various modifications, additions, changes and applications other than those specifically mentioned herein will be readily apparent to those having normal skill in the art without departing from the spirit of this invention.

What is claimed is:

1. Apparatus for providing an electrical interconnection between a patient and electrical medical measurement equipment comprising:

an electrode assembly including a substantially flexible housing of electrically insulating material having a flat surface, an electrical conductor with a flat surface embedded and wholly contained within said housing with said flat surface thereof externally exposed from said housing so as to form a continuous coplanar flat surface with the flat surface of said flexible housing, and a conductive lead extending from said housing in electrical communication with said conductor, for completing an electrical circuit to the measurement equipment by extension from said housing through a surface other than said coplanar flat surface, a detachable, disposable pad assembly including an annular body composed of a flexible, closed cell material having first and second parallel but oppositely disposed, substantially flat surfaces with a central bore extending therethrough, double adhesive surfaced disc means adhered to said first surface in surrounding relation to said bore and adhesively secured to said coplanar flat surface for releasably securing said pad assembly to said electrode assembly in proximity to said body with said flat conductor surface overlaying said bore, and an adhesive layer across substantially all of said second surface in surrounding relation to said bore adapted for retaining said pad assembly on the skin of the patient, and electrically conductive gelatinous means filling said bore for providing a relatively constant, low resistance electrical circuit between the skin of the patient in proximity to said bore and said electrical conductor surface, said gelatinous means being of a normal thickness greater than that of said pad assembly so as to be urged through an opening in said disc means into firm engagement with the exposed portion of said conductor on the flat surface of said housing when said pad assembly is applied to the skin of the patient thereby establishing an electrical interface between the patient and the medical measurement equipment while permitting both effective cleaning of said electrode assembly and disposal of said pad assembly and said gelatinous means thereafter.

2. Apparatus in accordance with claim 1 werein said disc means includes a thin disc having an outer perimeter configured in conformity to the outer perimeter of said electrode assembly housing, housing assembly flat surface and a central hole smaller in diameter than said pad assembly central bore for retaining said gelatinous means within said pad assembly bore while permitting electrical communication between said gelatinous means and said conductor surface, said disc having adhesive layers on both sides thereof for receiving said electrode assembly flat surface and said first surface of said body.

3. Apparatus in accordance with claim 2 wherein said gelatinous means is defined by an insert of porous open celled material permeated with an electrically conductive gelatin, said insert having a width less than the width of said pad assembly bore and a thicknes greater than said body thickness.

4. Apparatus in accordance with claim 1 wherein the perimeter of said pad assembly body defines a generally triangular shape, and the perimeter of said electrode assembly housing defines a generally circular shape dimensioned for fitting within the perimeter of said body triangular shape.

5. Apparatus in accordance with claim 1 wherein said pad assembly further includes a pair of thin discs each completely saturable by said electrically conductive gelatinous means and each having a greater width than said body central bore, said thin discs being positioned in enclosing relation across respective openings of said body central bore for retaining said electrically conductive gelatinous means therein.

6. In apparatus for providing an electrical interconnection between a patient and medical equipment for detecting electrical parameters, wherein an electrode assembly includes a substantially flexible circular shaped housing of electrically insulating material having a first substantially flat surface on one side and a second surface on the other side parallel to said first surface, an electrically conductive pellet embedded within said housing and having a flat surface area externally exposed from said housing as a central portion of said housing first flat surface so that said housing first flat surface and said pellet flat surface form a flush continuous surface, and an electrically conductive lead embedded at one end in said housing in electrical communication with said pellet and extending from said second surface of said housing for connection to the medical equipment, the combination therewith of:

a disposable pad assembly including a triangular shaped base frame of pliable, closed cell material having first and second parallel surfaces with an external perimeter greater than the external perimeter of said circular housing, a bore extending through said base frame between said parallel surfaces thereof, an adhesive means across substantially all of said second surface of said base frame for removable attachment to a patient's skin, and a relatively thin and flexible disc in the form of a double adhesive surfaced material having an adhesive coating on one side affixing said disc to said first parallel surface and having an outer perimeter conforming to the outer perimeter of said electrode assembly housing and a central opening therethrough which is axially aligned with and smaller than the width of said base frame bore, and said disc also having an adhesive coating on its opposite side detachably connecting said disc to said flush continuous surface of said electrode assembly with said exposed flat surface of said electrically conductive pellet in axial alignment and communication with said base frame bore and said central opening in said disc, and carrier of open celled material saturably filled with an electrically conductive gelatin, said carrier having a width greater than said disc opening but less than said base frame bore and further having a thickness greater than the depth of said base frame bore, said carrier being permanently retained within said base frame bore by the extension of said disc over said bore, said carrier being of a compressibility such that the removable adhesive attachment of said second surface of said base frame to a patient and said electrode assembly first flat surface detachably adhered to said disc will provide sufficient confining compression of said carrier so that said carrier completely fills both said base frame bore and is urged through said central disc opening causing said electrically conductive gelatin to contact both the patient's skin and said conductive pellet for effecting a constant, low resistance electric circuit between the patient and said pellet flat surface.

. A disposable pad assembly for electrically interfacbetween a patient and an electrode adapted for :trical communication with medical monitoring or isuring equipment wherein the electrode has an in:onnecting flat surface including an outer area of :trically insulating material in surrounding relation n inner area of electrically conductive material coming:

body portion of pliable, closed cell material having first and second parallel flat surfaces and a central bore therethrough between said surfaces, relatively thin, flexible disc fabricated of different material than said body portion with an outer periphery conforming to the outer periphery of said interconnecting flat surface of said electrode and a central hole therethrough, said disc being affixed on one side to said first parallel flat surface of said body portion with said central hole in said disc axially aligned with said central bore in said body portion, first adhesive coating on the other side of said disc in surrounding relation to said central hole for detachably securing the flat surface of said electrode to said body portion with the electrically conductive inner area of said electrode aligned with at least a portion of the opening of said bore, a second adhesive coating covering substantially all of said second surface on surrounding relation to said bore for detachably securing said body portion to the skin of a patient, an electrically conductive gelatin in said bore positioned to contact and establish electrical communication between both said electrically conductive inner area of said electrode interconnecting flat surface and the patient's skin under said bore when said body portion and disc are detachably connected to said electrode and to a patient's skin, and means retaining said gelatin in said bore.

8. A disposable pad assembly in accordance with claim 7 wherein said central hole in said disc is smaller in diameter than the opening of said bore, and wherein said gelatin retaining means includes a carrier of an open celled, reticulated material having continuous passageways therethrough saturably receiving said gelatin, said carrier having a width greater than said central hole but less than the width of said bore so that said carrier is held within said bore by adhesive engagement with the portion of said disc extending over said bore, said carrier further having a thickness greater than the thickness of said body portion so that said carrier and said gelatin therewithin effectively fills said bore and said central hole in response to confining compression of said carrier within said bore whenever said body portion is removably secured to the skin of a patient.

9. A disposable pad assembly in accordance with claim 7 wherein said central hole in said disc is larger than the opening of said bore, and wherein said gelatin retaining means includes a pair of thin discs of gelatin saturable material permanently attached to said first and second parallel flat surfaces of said body portion, respectively, across the respective openings of said bore, the thin disc of gelatin saturable material which is attached to said first parallel flat surface being substantially within said central hole such that it will not interfere with the detachable connection of said disc and body portion with said interconnecting flat surface of said electrode while allowing said gel to establish electrical contact with said electrically conductive material in said electrode.

10. A disposable pad assembly in accordance with claim 9 wherein said gelatin retaining means further includes a carrier of an open celled, reticulated material filling said body portion bore between said thin discs of gelatin saturable material.

11. A disposable pad assembly in accordance with claim 7 wherein the perimeter of said body portion is a substantially triangular-shaped configuration.

* * * * *